(12) United States Patent
Flanagan

(10) Patent No.: US 8,337,878 B2
(45) Date of Patent: Dec. 25, 2012

(54) MEDICAL DEVICES HAVING COATINGS FOR THERAPEUTIC AGENT DELIVERY

(75) Inventor: Aiden Flanagan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 470 days.

(21) Appl. No.: 12/544,679

(22) Filed: Aug. 20, 2009

(65) Prior Publication Data
US 2010/0055151 A1 Mar. 4, 2010

Related U.S. Application Data

(60) Provisional application No. 61/092,355, filed on Aug. 27, 2008.

(51) Int. Cl.
*A61F 2/00* (2006.01)
(52) U.S. Cl. ....................................................... 424/426
(58) Field of Classification Search ........................ None
See application file for complete search history.

(56) References Cited

U.S. PATENT DOCUMENTS

| | | | |
|---|---|---|---|
| 6,545,097 B2 | 4/2003 | Pinchuk et al. | |
| 6,712,845 B2* | 3/2004 | Hossainy | 623/1.42 |
| 2004/0148015 A1* | 7/2004 | Lye et al. | 623/1.15 |
| 2004/0186553 A1 | 9/2004 | Yan | |
| 2007/0048452 A1 | 3/2007 | Feng et al. | |
| 2007/0224235 A1* | 9/2007 | Tenney et al. | 424/423 |
| 2007/0255393 A1 | 11/2007 | Flanagan | |
| 2008/0188836 A1 | 8/2008 | Weber et al. | |
| 2009/0081272 A1 | 3/2009 | Clarke et al. | |
| 2009/0123521 A1* | 5/2009 | Weber et al. | 424/426 |

FOREIGN PATENT DOCUMENTS

| | | |
|---|---|---|
| EP | 0875218 A2 | 11/1998 |
| EP | 1764116 A1 | 3/2007 |
| WO | 2007108916 A2 | 9/2007 |

* cited by examiner

*Primary Examiner* — Suzanne Ziska
(74) *Attorney, Agent, or Firm* — Mayer & Williams PC; David B. Bonham; Keum J. Park

(57) ABSTRACT

According to an aspect of the invention, implantable and insertable medical devices are provided that include (a) a substrate, (b) a porous layer comprising interconnected pores disposed over the substrate, (c) at least one first therapeutic agent disposed within and/or beneath the porous layer, (d) a composite layer disposed over the porous layer that includes (i) at least one therapeutic agent eluting region containing at least one second therapeutic agent and at least one matrix material and (ii) at least one bioerodible region containing at least one bioerodible material that extends from the surface of the composite layer to the porous layer.

20 Claims, 2 Drawing Sheets

MEDICAL DEVICES HAVING COATINGS FOR THERAPEUTIC AGENT DELIVERY

RELATED APPLICATIONS

This application claims priority from U.S. provisional application 61/092,355, filed Aug. 27, 2008, which is incorporated by reference herein in its entirety.

TECHNICAL FIELD

This invention relates to medical devices, and more particularly, to medical devices having coatings that allow for the release of underlying therapeutic agents.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

For example, in recent years, drug eluting coronary stent systems, which are commercially available from Boston Scientific Corp. (TAXUS, PROMUS), Johnson & Johnson (CYPHER) and others, have been widely used for maintaining vessel patency after balloon angioplasty. These products are based on metallic expandable stents with polymer coatings that release antirestenotic drugs at a controlled rate and total dose.

SUMMARY OF THE INVENTION

According to an aspect of the invention, medical devices are provided that comprise (a) a substrate, (b) a porous layer comprising interconnected pores disposed over the substrate, (c) a first therapeutic agent disposed within and/or beneath the porous layer, (d) a composite layer over the porous layer that comprises (i) a therapeutic agent eluting region that comprises a second therapeutic agent and a matrix material and (ii) a bioerodible region, comprising a bioerodible material and extending from the surface of the composite layer to the porous layer.

Other aspects of the invention relate to methods for forming such medical devices.

An advantage of the present invention is that medical devices may be provided, in which the release of therapeutic agents is controlled and selectively administered.

These and other aspects, embodiments and advantages of the present invention will become immediately apparent to those of ordinary skill in the art upon review of the Detailed Description and Claims to follow.

DETAILED DESCRIPTION

Figure 1A:
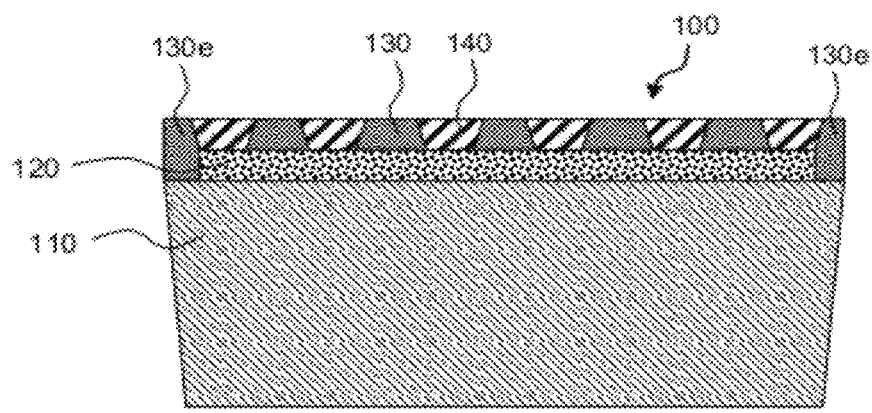
FIG. 1A is a schematic cross-sectional view of a stent strut in accordance with an embodiment of the present invention.

According to an aspect of the invention, implantable and insertable medical devices are provided that include (a) a substrate, (b) a porous layer comprising interconnected pores disposed over the substrate, (c) at least one first therapeutic agent disposed within and/or beneath the porous layer, (d) a composite layer disposed over the porous layer that includes (i) at least one therapeutic agent eluting region, which contains at least one second therapeutic agent and at least one matrix material and (ii) at least one bioerodible region, which contains at least one bioerodible material, extending from the surface of the composite layer to the porous layer.

In certain embodiments, an optional barrier region (e.g., in the form of a barrier layer, etc.) is provided between the porous layer and the at least one therapeutic agent eluting region.

As used herein a "layer" is a three-dimensional structure whose thickness is small compared to both its length and width (e.g., its length and width are each at least four times as great as its thickness). Terms such as "film," "layer" and "coating" may be used interchangeably herein. As used herein a layer need not be planar, for example, taking on the contours of an underlying structure. A layer can be discontinuous, providing only partial coverage of an underlying structure (e.g., made up of a collection of two or more, sometimes many more, material regions). For example, a discontinuous layer may be provided over an underlying structure in a desired pattern using a suitable applicator (e.g., ink jet device, pen, brush, roller, etc.) or using a suitable masking technique.

"Therapeutic agents," "pharmaceutically active agents," "pharmaceutically active materials," "drugs," "biologically active agents" and other related terms may be used interchangeably herein and include genetic therapeutic agents, non-genetic therapeutic agents and cells. A wide variety of therapeutic agents can be employed in conjunction with the present invention including those used for the treatment of a variety of diseases and conditions.

In certain embodiments, the first and second therapeutic agents may be selected from endothelial cell growth promoters, antithrombotic agents, vasodilators, anti-restenotic agents, anti-proliferative agents, antimicrobial agents, analgesic agents, anti-inflammatory agents, and combinations thereof.

Therapeutic agents can be incorporated into the structures of the invention in various ways. For example, at least one therapeutic agent may be included in a deposition material that is used to form a given region of material, thereby incorporating the therapeutic agent in the material at the time of formation. As another example, a composition containing at least one therapeutic agent (e.g., a powder, a solution, a liquid suspension) and any optional additional materials (e.g., solvent species, etc.) may be applied to pre-existing region of material (e.g., a porous layer, solvent swellable layer, etc.).

Substrate materials, porous layer materials, matrix materials, bioerodible materials and optional barrier region materials may vary widely in composition and are not limited to any particular material, except that the materials forming the bioerodible region(s) is/are selected such that the bioerodible region(s) bioerode at a faster rate than other materials, particularly the substrate materials and matrix materials, assuming that the other materials bioerode at all (i.e., they may be bioerodible or biostable).

As used herein, a "bioerodible" material is one that is eventually removed from the device in vivo due to one or more erosion processes (e.g., dissolution, biodegradation, oxidation, etc.).

Substrate materials, porous layer materials, matrix materials, and bioerodible materials may be selected, for example, from (a) organic materials (i.e., materials containing organic species, typically 50 wt % or more, for example, from 50 wt % to 75 wt % to 90 wt % to 95 wt % to 97.5 wt % to 99 wt % or more) such as polymeric materials (i.e., materials containing polymers, typically 50 wt % or more polymers, for example, from 50 wt % to 75 wt % to 90 wt % to 95 wt % to 97.5 wt % to 99 wt % or more) and biologics, (b) inorganic materials (i.e., materials containing inorganic species, typically 50 wt % or more, for example, from 50 wt % to 75 wt % to 90 wt % to 95 wt % to 97.5 wt % to 99 wt % or more), such as metallic inorganic materials (i.e., materials containing metals, typically 50 wt % or more, for example, from 50 wt % to 75 wt % to 90 wt % to 95 wt % to 97.5 wt % to 99 wt % or more) and non-metallic inorganic materials (i.e., materials containing non-metallic inorganic materials, typically 50 wt % or more, for example, from 50 wt % to 75 wt % to 90 wt % to 95 wt % to 97.5 wt % to 99 wt % or more) (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic hybrids, polymer/ceramic hybrids, etc.).

Specific examples of inorganic non-metallic materials may be selected, for example, from materials containing one or more of the following: metal oxide ceramics, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic materials may be selected, for example, from metals such as gold, iron, niobium, platinum, palladium, iridium, osmium, rhodium, titanium, tantalum, tungsten, ruthenium, zinc, and magnesium, among others, and alloys such as those comprising iron and chromium (e.g., stainless steels, including platinum-enriched radiopaque stainless steel), niobium alloys, titanium alloys, alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and bioerodible alloys including alloys of magnesium, zinc and/or iron (and their alloys with combinations of Ce, Ca, Al, Zr, La and Li), among others (e.g., alloys of magnesium including its alloys that comprises one or more of Fe, Ce, Al, Ca, Zn, Zr, La and Li, alloys of iron including its alloys that comprise one or more of Mg, Ce, Al, Ca, Zn, Zr, La and Li, alloys of zinc including its alloys that comprise one or more of Fe, Mg, Ce, Al, Ca, Zr, La and Li, etc.).

Specific examples of organic materials include polymers (biostable or bioerodible) and other high molecular weight organic materials, and may be selected, for example, from suitable materials containing one or more of the following, among others: polycarboxylic acid homopolymers and copolymers including polyacrylic acid, alkyl acrylate and alkyl methacrylate homopolymers and copolymers, including poly(methyl methacrylate-b-n-butyl acrylate-b-methyl methacrylate) and poly(styrene-b-n-butyl acrylate-b-styrene) triblock copolymers, polyamides including nylon 6,6, nylon 12, and polyether-block-polyamide copolymers (e.g., Pebax® resins), vinyl homopolymers and copolymers including polyvinyl alcohol, polyvinylpyrrolidone, polyvinyl halides such as polyvinyl chlorides and ethylene-vinyl acetate copolymers (EVA), vinyl aromatic homopolymers and copolymers such as polystyrene, styrene-maleic anhydride copolymers, vinyl aromatic-alkene copolymers including styrene-butadiene copolymers, styrene-ethylene-butylene copolymers (e.g., a poly(styrene-b-ethylene/butylene-b-styrene (SEBS) copolymer, available as Kraton® G series polymers), styrene-isoprene copolymers (e.g., poly(styrene-b-isoprene-b-styrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as poly (styrene-b-isobutylene-b-styrene) or SIBS, which is described, for instance, in U.S. Pat. No. 6,545,097 to Pinchuk et al.), ionomers, polyesters including polyethylene terephthalate and aliphatic polyesters such as homopolymers and copolymers of lactide (which includes d-,l- and meso-lactide), glycolide (glycolic acid) and epsilon-caprolactone, polycarbonates including trimethylene carbonate (and its alkyl derivatives), polyanhydrides, polyorthoesters, polyether homopolymers and copolymers including polyalkylene oxide polymers such as polyethylene oxide (PEO) and polyether ether ketones, polyolefin homopolymers and copolymers, including polyalkylenes such as polypropylene, polyethylene, polybutylenes (such as polybut-1-ene and polyisobutylene), polyolefin elastomers (e.g., santoprene) and ethylene propylene diene monomer (EPDM) rubbers, fluorinated homopolymers and copolymers, including polytetrafluoroethylene (PTFE), poly(tetrafluoroethylene-co-hexafluoropropene) (FEP), modified ethylene-tetrafluoroethylene copolymers (ETFE) and polyvinylidene fluoride (PVDF), silicone homopolymers and copolymers including polydimethylsiloxane, polyurethanes, biopolymers such as polypeptides, proteins, polysaccharides, fibrin, fibrinogen, collagen, elastin, chitosan, gelatin, starch, and glycosaminoglycans such as hyaluronic acid; as well as blends and further copolymers of the above.

Examples of medical devices benefiting from the present invention vary widely and include implantable or insertable medical devices, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglielmi detachable coils and metal coils), septal defect closure devices, myocardial plugs, patches, electrical stimulation leads, including leads for pacemakers, leads for implantable cardioverter-defibrillators, leads for spinal cord stimulation systems, leads for deep brain stimulation systems, leads for peripheral nerve stimulation systems, leads for cochlear implants and leads for retinal implants, ventricular assist devices including left ventricular assist hearts and pumps, total artificial hearts, shunts, valves including heart valves and vascular valves, anastomosis clips and rings, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, ocular implants, dental implants, or other devices that are implanted or inserted into the body and from which therapeutic agent is released.

The medical devices of the present invention thus include, for example, implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Subjects are vertebrate subjects, more typically mammalian subjects, including human subjects, pets and livestock.

Figure 1B:
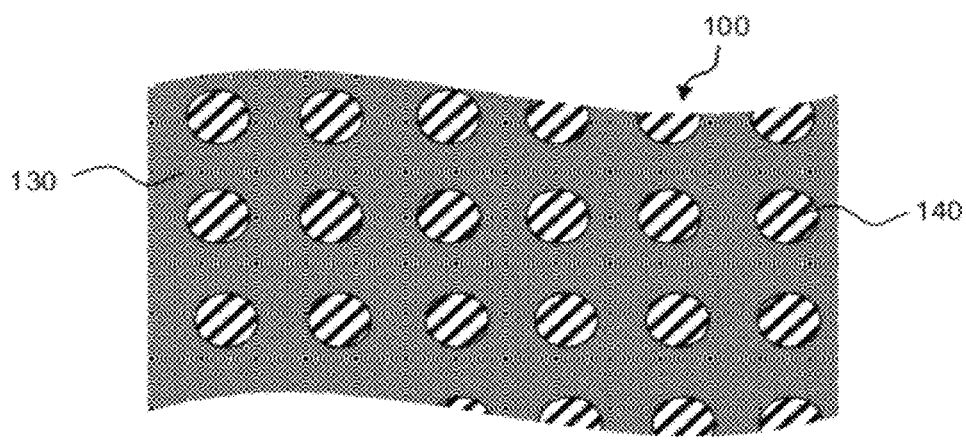
FIG. 1B is a schematic partial top view of the stent strut of FIG. 1A.

In certain embodiments, the medical device is a stent, although the invention clearly is not so-limited. Referring now to FIG. 1A, there is shown a schematic cross-sectional view of a stent strut 100, in accordance with an embodiment of the present invention. FIG. 1B is a schematic partial top view of the stent strut 100 of FIG. 1A. The stent strut 100 of FIGS. 1A and 1B includes a substrate (e.g., stainless steel, nitinol, etc.), which in this embodiment gives the medical device desirable mechanical characteristics, particularly strength. Disposed over the abluminal surface (i.e., outer blood vessel contacting surface) of the substrate 110 is a porous layer 120 (e.g., an organic, inorganic or organic/inorganic hybrid porous layer), which comprises interconnected pores, and within which a first therapeutic agent (e.g., an antithrombotic agent, a growth factor, etc.) is disposed. Over the porous layer 120 is a composite layer containing a therapeutic agent eluting region 130 and a plurality of bioerodible regions 140. The bioerodible regions 140 may be, for example, between 10 and 50 microns in width, among other values, and comprise a bioerodible material (e.g., an organic, inorganic or organic/inorganic hybrid bioerodible material). The therapeutic agent eluting region 130 comprises a second therapeutic agent (e.g., an anti-restenotic drug such as paclitaxel or an olimus family drug such as sirolimus, everolimus, etc.) and a matrix material (e.g., an organic, inorganic or organic/inorganic hybrid matrix material). The therapeutic agent eluting region 130 forms apertures that extend through the thickness of the region 130, which apertures are occupied by the bioerodible regions 140. Upon bioerosion of a given region of bioerodible material 140, the resulting open aperture is able to act as a passageway for the elution of the first therapeutic agent from the porous layer 120 surface to the exterior of the device. To prevent elution of the first therapeutic agent from edges of the porous layer 120, the therapeutic agent eluting region 130 is extended down to the substrate 110 at the edges of the stent strut 100, as shown by numerals 130e in FIG. 1A.

Figure 2:
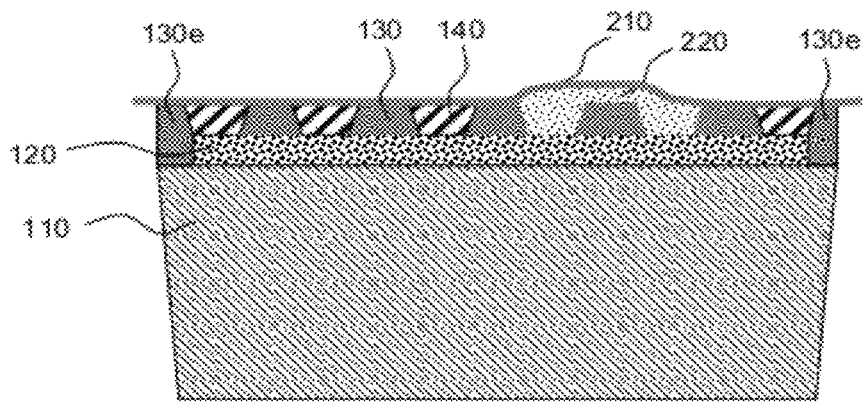
FIG. 2 is a schematic cross-sectional view of a stent strut in accordance with the present invention, which is in partial contact with a blood vessel wall.

This is schematically illustrated, for example, in FIG. 2 which illustrates the stent strut like that of FIG. 1A in contact with a blood vessel 210. Also shown is a region 220 where the stent strut has non-apposition with (i.e., does not contact) the blood vessel. There is a higher possibility of thrombus forming in such areas. In the stent of the present invention, the bioerodible regions 140 in the non-apposed part of the stent strut erode faster that the bioerodible regions 140 in the remainder of the strut, which are properly positioned against the blood vessel 210. This bioerosion process exposes the porous layer 120 to the environment at the exterior of the device, in particular, to the cavity where the stent strut is not in apposition with the blood vessel, allowing elution of the first therapeutic agent into the cavity, which may be, for example, an anti-thrombotic drug such as heparin (to prevent thrombotic events) or a cell-growth-promoting drug such as VEGF (which can be eluted to encourage endothelial and/or smooth muscle cell growth to fill the cavity between the stent and the vessel wall). Because the porous layer 120 comprises an interconnecting series of pores, the first therapeutic agent can diffuse from those regions of the porous layer 120 that remain under intact regions of bioerodible material 140 into those regions of the porous layer 120 where the bioerodible material 140 has been removed. Thus, the porous layer 120 may act as a single large reservoir for the first therapeutic agent in certain embodiments.

Bioerosion of the bioerodible material 140 is not necessary, however, for the elution of the second drug (e.g., an anti-restenotic drug) from the therapeutic agent eluting layer 130, as this layer is exposed to the biological environment from the time of stent placement.

Figure 3:
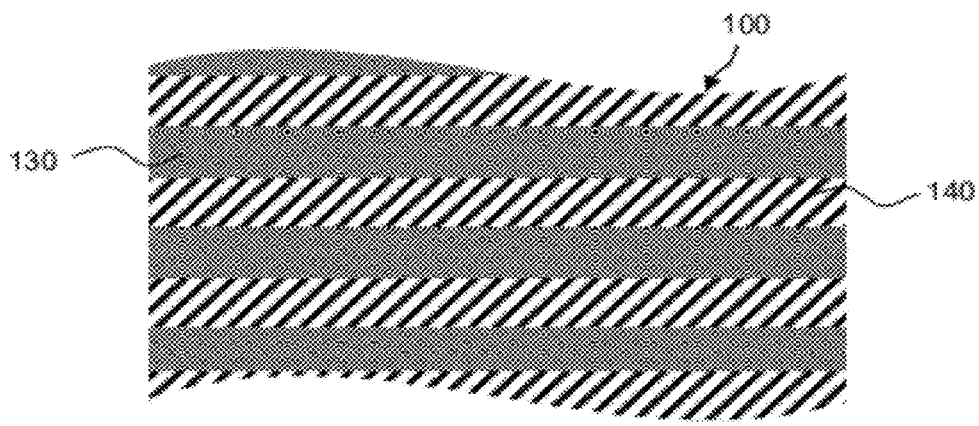
FIG. 3 is a schematic partial top view of a stent strut, in accordance with another embodiment of the present invention.
Figure 4:
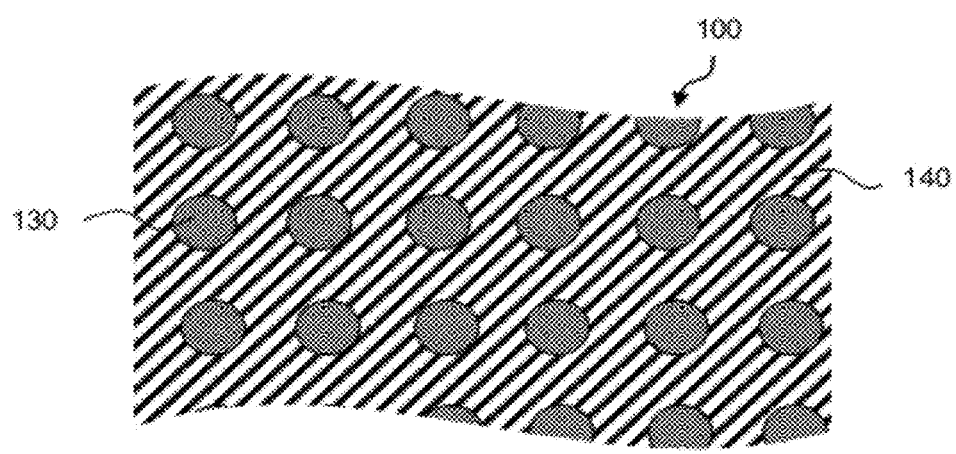
FIG. 4 is a schematic partial top view of a stent strut, in accordance with yet another embodiment of the present invention.

In the embodiment of FIGS. 1A and 1B, the composite layer comprises a single therapeutic agent eluting region 130 and a plurality of bioerodible regions 140. In other embodiments, for example, as shown in the schematic partial top view of FIG. 3, a plurality of therapeutic agent eluting regions 130 and a plurality of bioerodible regions 140 may be employed. In still other embodiments, for example, as shown in the schematic partial top view of FIG. 4, a plurality of therapeutic agent eluting regions 130 and a single bioerodible region 140 may be employed.

Figure 5:
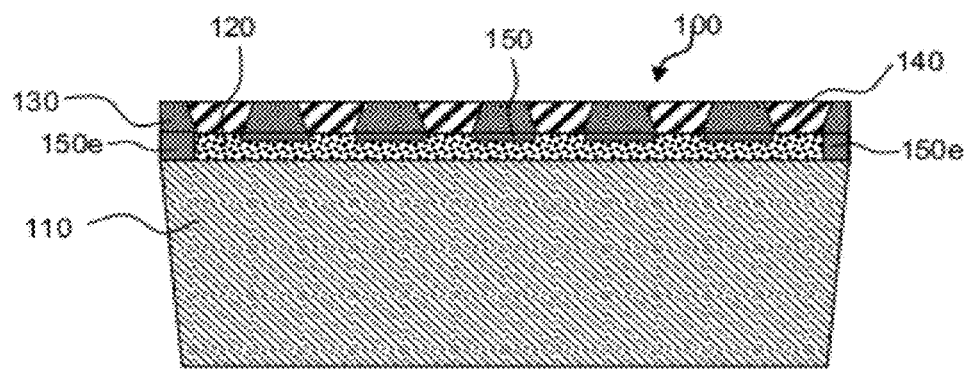
FIG. 5 is a schematic cross-sectional view of a stent strut in accordance with another embodiment the present invention.

Depending upon the propensity of the first therapeutic agent to diffuse through the therapeutic agent eluting layer (if any), in some embodiments, it may be desirable to include a barrier region between the porous layer and the therapeutic agent eluting layer. For example, FIG. 5 is like FIG. 1A in that it shows a substrate 110, a porous layer 120, and composite layer comprising a therapeutic agent eluting region 130, having apertures which extend through the thickness of the drug eluting layer 130 and which are filled with regions of bioerodible material 140. Unlike FIG. A1, however, the device of FIG. 5 further provides a barrier region 150 (e.g., an organic, inorganic or organic/inorganic hybrid barrier region) between the porous layer 120 and the therapeutic agent eluting region 130 to reduce or prevent transport (i.e., movement) of the first therapeutic agent from the porous layer 120 into the therapeutic agent eluting layer 130. Moreover, to prevent elution of the first therapeutic agent from edges of the porous layer 120, the barrier region 150 is extended down to the substrate 110 at the edges of the stent strut 100, as shown by numerals 150e in FIG. 5.

For a stent, specific examples of substrate materials include (a) biostable metals such as stainless steel, including platinum enriched stainless steel (PERSS), Nitinol alloys, and cobalt chromium alloys, (b) bioerodible metals such as Mg, Fe, Zn and their alloys, and (c) bioerodible polymers such as polylactide and poly(lactide-co-glycolide).

Methods of forming stent substrates include molding techniques as well as cutting techniques in which a tube of material is cut, for example, with a blade or an energetic beam (e.g., with a laser). Such a tube may be cut, for example, prior to adding the additional layers described herein or after such layers have been added to the tubular substrate. Typically, the various layers are disposed such that the porous layer is not disposed at the edge of the stent.

Porous layers in the devices of the present invention include nanoporous, microporous, mesoporous, and macroporous layers. As used herein a "porous" layer is a layer that contains pores. A "nanoporous layer" is a layer that contains nanopores. A "microporous layer" is a layer that contains micropores. A "mesoporous layer" is a layer that contains mesopores. A "macroporous layer" is a layer that contains macropores. In accordance with the International Union of Pure and Applied Chemistry (IUPAC), a "nanopore" is a pore having a width that does not exceed 50 nm (e.g., from 0.5 nm or less to 1 nm to 2.5 nm to 5 nm to 10 nm to 25 nm to 50 nm), and this definition is used herein. As used herein, nanopores include "micropores," which are pores having a width that does not exceed 2 nm, and "mesopores," which are range from 2 to 50 nm in width. As used herein, "macropores" are larger than 50 nm in width and are thus not nanopores.

Specific examples of materials for forming porous layers in accordance with the present invention include a wide range of the organic, inorganic and organic/inorganic hybrid materials which may be selected from those described above. In certain embodiments, materials for forming porous layers in accordance with the present invention are selected from those described above for use as substrate materials for stents, as well as biostable polymers, metal oxides, semi-metal (e.g., silicon, germanium) oxides and carbon.

Porous layer thicknesses may vary widely, typically ranging from 100 nm to 1000 nm (1 μm) to 10000 nm (10 μm) or more in thickness.

Where one or more first therapeutic agents are provided within the porous layer, the porous layer may contain, for example, from 1 wt % or less to 2 wt % to 5 wt % to 10 wt % to 25 wt % or more of a single first therapeutic agent or of a mixture of first therapeutic agents within the layer.

Methods of forming porous layers include Argon ion bombardment (e.g., for materials such as metals), laser patterning (e.g., for materials such as polymers, metals and ceramics), sol-gel processing (e.g., for metal oxides and semi-metal oxides), and methods for forming porous carbon coatings such as those described in US 2007/0255393 to Flanagan, among others.

Methods of forming porous layers in accordance with the present invention also include electrostatic spray ("electrospray") coating processing, particularly where polymeric layers of interconnected polymeric particles are deposited. Information on electrospray processing may be found, for example, in Pub. No. U.S. 2007/0048452 to Feng et al.

Methods of forming porous layers in accordance with the present invention further include those wherein nanoparticles are created, accelerated and directed onto the upper surface of a structure, thereby forming an inorganic layer over the structure. (As used herein, a "nanoparticle" is a particle having a width that does not exceed 1 μm, for example, ranging from 10 nm or less to 25 nm to 50 nm to 100 nm to 250 nm to 500 nm to 1000 nm in width.) For example, in some embodiments, the nanoparticles are charged nanoparticles, which are accelerated onto a structure surface by subjecting them to an electric field. The trajectory of the nanoparticles may be further influenced through the use of a secondary electric field or a magnetic field, where desired. Without wishing to be bound by theory, when nanoparticles are accelerated towards a surface, melting can be induced upon landing by imparting them with sufficient kinetic energy. For example, in embodiments where charged nanoparticles are accelerated using an electric field, a low applied voltage will create a small electric field which lands them on the substrate with little or no thermal effects. Higher applied voltages, however, will result in greater field strengths, which if sufficiently great will result in a transformation of kinetic energy into heat in an amount sufficient to melt the nanoparticles slightly together, leaving gaps between the particles. Even higher field strengths will solidify the individual particles into a solid material without gaps.

As a specific example, a system for performing nanoparticle deposition along the lines described above is available from Mantis Deposition Ltd., Thame, Oxfordshire, United Kingdom, who market a high-pressure magnetron sputtering source which is able to generate nanoparticles from a sputter target with as few as 30 atoms up to those with diameters exceeding 15 nm. (A system similar to the Mantis system can be obtained from Oxford Applied Research, Witney, Oxon, UK.) This system is operated at about $5 \times 10^{-5}$ mbar, although the precise operating pressure used will vary widely, depending on the specific process and system that is employed, among other factors. The size of the nanoparticles is affected by several parameters, including the nanoparticle material, the distance between the magnetron surface and the exit aperture (e.g., larger distances have been observed to create larger nanoparticles), gas flow (e.g., higher gas flows have been observed to create smaller nanoparticle sizes), and gas type (e.g., helium has been observed to produce smaller particles than argon). Systems like the Mantis Deposition Ltd. system can produce nanoparticles, a large fraction of which of which (approximately 40% to 80%) have a charge of one electron. Consequently, a magnetic field or a secondary electric field can be used to separate particles of similar weight from one another (because lighter particles are deflected to a greater degree in a given field than are the larger particles of the same charge). For example, the above Mantis Deposition Ltd. system is able to produce charged nanoparticle streams with a very narrow mass distribution. Moreover, it is possible to accelerate the negatively charged particles onto a positively biased surface in order to impact the particles on the surface with elevated kinetic energy. A positively biased grid may also be used to accelerate the particles, allowing the particles to pass through holes in the grid and impinge on the surface. By altering the bias voltage from low to high values the deposited film changes from porous loosely bound nanoparticles to a solid film of metal. Due to the fact that the amount of energy needed to melt the individual nanoparticles is relatively low compared to the energy needed to increase the bulk temperature of an underlying structure, this process is effectively performed at or near room temperature.

As indicated above, disposed over the porous layer is a composite layer that includes (i) one or more therapeutic agent eluting regions and (ii) one or more bioerodible regions, which bioerodible regions extend from the surface of the composite layer to the top surface of the porous layer.

The one or more therapeutic agent eluting regions include at least one second therapeutic agent and at least one matrix material, which forms, for example, a porous or non-porous matrix that allows for the release of the second therapeutic agent.

The therapeutic agent eluting regions may vary widely in thickness, typically ranging from 100 nm to 1000 nm (1 µm) to 10000 nm (10 µm) or more in thickness.

Therapeutic agent eluting regions may contain, for example, from 1 wt % or less to 2 wt % to 5 wt % to 10 wt % to 25 wt % to 50 wt % or more of a single second therapeutic agent or of a mixture of second therapeutic agents within the regions.

Therapeutic agent eluting regions may contain, for example, from 50 wt % or less to 75 wt % to 90 wt % to 95 wt % to 97.5 wt % to 99 wt % or more of a single matrix material or a mixture of matrix materials within the regions.

Specific examples of matrix materials for forming therapeutic agent eluting regions in stents include a wide range of the organic, inorganic and organic/inorganic hybrid materials which may be selected from those described above, among others.

In certain embodiments, matrix materials for forming therapeutic agent eluting regions in stents include biostable and bioerodible polymers, for example, biostable polymers such as styrene-isobutylene copolymers and vinylidene fluoride-hexafluoropropylene copolymers, and biodegradable polymers such as polylactide or poly(lactide-co-glycolide).

Methods for forming therapeutic agent eluting regions based on the above and other matrix materials include solvent based techniques (e.g., where the matrix materials are dissolvable, and the therapeutic agent is dissolvable/dispersible, in a given solvent) and thermoplastic processing techniques (e.g., where the matrix materials have thermoplastic character and the therapeutic agent is sufficiently robust to endure the processing temperatures). The solutions, dispersions and melts formed using such techniques may be applied to an underlying structure using various techniques, including dipping, extrusion, spraying, spin coating, electrospun coating, web coating, and direct application techniques (e.g., techniques that employ an application device such as roller, brush, pen, pipette or ink jet printer, among others).

As elsewhere herein, masking techniques and direct application techniques may be employed where it is desired to form patterned layers such that certain surfaces of the underlying structure are selectively coated, but not others.

As noted above, the materials forming the one or more bioerodible regions of the composite layer are selected such that the bioerodible regions bioerode at a faster rate than other materials, particularly the substrate materials and matrix materials, assuming that such other materials bioerode at all (i.e., they may be bioerodible or biostable).

Bioerodible regions in accordance with the invention include at least one bioerodible material. Bioerodible regions in accordance with the invention include a wide range of organic, inorganic and organic/inorganic hybrid materials which may be selected from those described above, among others. Specific examples of bioerodible materials for use in stents include bioerodible organic and inorganic materials, for example, bioerodible polymers such as bioerodible polyesters, bioerodible polyorthoesters and bioerodible polyanhydrides, for example, poly(lactide), poly(glycolide) and poly(lactide-co-glycolide) (PLGA), particularly low molecular weight PLGA, bioerodible ceramics and bioerodible metals such as Mg, Fe, Zn and their alloys.

Methods for forming regions of polymeric bioerodible regions include solution-based and thermoplastic techniques such as those described above, among others. Methods for forming inorganic bioerodible regions include inorganic nanoparticle deposition (see, e.g., the Mantis system discussed above) and various physical vapor deposition (PVD) techniques such as those described below, among others.

As elsewhere herein, masking techniques and direct application techniques may be employed where it is desired to form patterned layers such certain surfaces of the underlying structure are selectively coated, but not others.

For example, one or more therapeutic agent eluting regions (e.g., a patterned therapeutic agent eluting layer with apertures) may be deposited first, followed by deposition of one or more bioerodible regions in those regions that are not coated by the therapeutic agent eluting regions (e.g., within the apertures). Conversely, one or more bioerodible regions may be deposited first, followed by deposition of one or more therapeutic agent eluting regions.

As indicated above, in some embodiments, bioerodible regions may be formed via vapor deposition methods, including PVD processes. PVD processes are processes in which a source of material, typically a solid material, is vaporized, and transported to a structure upon which a film (i.e., a layer) of the material is formed. PVD processes are generally used to deposit films with thicknesses in the range of a few nanometers to thousands of nanometers, although greater thicknesses are possible. PVD is typically carried out under vacuum (i.e., at pressures that are less than ambient atmospheric pressure). Some specific PVD methods that are used to form bioerodible regions in accordance with the present invention include evaporation, sublimation, sputter deposition and laser deposition. For instance, in some embodiments, at least one source material is evaporated or sublimed, and the resultant vapor travels from the source to a substrate, resulting in a deposited layer on the substrate. Examples of sources for these processes include resistively heated sources, heated boats and heated crucibles, among others. Sputter deposition is another PVD process, in which surface atoms or molecules are physically ejected from a surface by bombarding the surface (commonly known as a "target") with high-energy ions. Ions for sputtering can be produced using a variety of techniques, including arc formation (e.g., diode sputtering), transverse magnetic fields (e.g., magnetron sputtering), and extraction from glow discharges (e.g., ion beam sputtering), among others. Pulsed laser deposition (PLD) is yet another PVD process, which is similar to sputter deposition, except that vaporized material is produced by directing laser radiation (e.g., pulsed laser radiation), rather than high-energy ions, onto the target material. As advantage of the PLD process is that films can be deposited upon substrates at or near room. Consequently, films can be formed over temperature-sensitive materials, for example, organic materials such as polymers and therapeutic agents.

As noted above, in certain embodiments, it may be desirable to include a barrier region between the porous layer and the therapeutic agent eluting layer in the devices of the invention. Examples of barrier materials include biostable and bioerodible inorganic, organic and inorganic/organic hybrid materials that substantially or completely block the transport of the first therapeutic agent. Examples of techniques for the application of barrier material layers include solvent-based and thermoplastic application techniques (e.g., for polymeric barrier regions) and PVD and nanoparticle based deposition techniques (e.g., for inorganic barrier regions).

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) a substrate, (b) a porous layer comprising interconnected pores disposed over the substrate, (c) a first therapeutic agent disposed within the porous layer, (d) a composite layer over the porous layer that comprises (i) a therapeutic agent eluting region that comprises a second therapeutic agent and a matrix material and (ii) a plurality of bioerodible regions comprising a bioerodible material, said bioerodible material extending from the surface of the composite layer to the porous layer, wherein the therapeutic agent eluting region is disposed at the surface of the composite layer, wherein bioerosion of said bioerodible regions exposes the porous layer lying under the bioerodible regions to an exterior of the device and allows elution of the first therapeutic agent from the device, and wherein the interconnected pores of the porous layer allow diffusion of the first therapeutic agent from a region of the porous layer lying under an intact bioerodible region to a region of the porous layer that is exposed due to said bioerosion.

2. The medical device of claim 1, wherein the substrate is selected from a bioerodible metallic substrate and a biostable metallic substrate.

3. The medical device of claim 1, wherein the porous layer is a macroporous layer.

4. The medical device of claim 1, wherein the porous layer comprises interconnected polymer particles or interconnected metallic particles.

5. The medical device of claim 1, wherein the first therapeutic agent is selected from an anti-thrombotic agent, a cell-growth-promoting agent, or a combination thereof.

6. The medical device of claim 1, wherein the matrix material is a polymer.

7. The medical device of claim 1, wherein the second therapeutic agent is an anti-restenotic agent.

8. The medical device of claim 1, wherein the bioerodible material is a bioerodible metal.

9. The medical device of claim 1, wherein the bioerodible material is a vapor deposited material.

10. The medical device of claim 1, wherein the composite layer comprises (a) a therapeutic agent eluting region in the form of a layer that comprises a plurality of apertures and (b) said plurality of bioerodible regions occupy the apertures.

11. The medical device of claim 10, wherein the apertures range from 10 to 50 microns in width.

12. The medical device of claim 1, wherein the composite layer comprises a plurality of therapeutic agent eluting regions.

13. The medical device of claim 1, further comprising a barrier region between the therapeutic agent eluting region and the porous layer.

14. The medical device of claim 1, wherein the medical device is a stent.

15. The medical device of claim 14, wherein the porous layer, the first therapeutic agent, and the composite layer are disposed on the abluminal surface of the stent.

16. The medical device of claim 14, wherein substrate, the porous layer, the composite layer are all bioerodible.

17. The medical device of claim 14, wherein the first therapeutic agent is selected from an anti-thrombotic agent, a cell-growth-promoting agent, or a combination thereof and wherein the second therapeutic agent is an anti-restenotic agent.

18. The medical device of claim 14, wherein the composite layer comprises a therapeutic agent eluting region in the form of a layer that comprises a plurality of apertures and wherein said plurality of bioerodible regions occupy the apertures.

19. The medical device of claim 14, wherein said substrate is formed of a bioerodible substrate material, wherein said matrix material is formed of a bioerodible matrix material, and wherein said bioerodible material bioerodes at a faster rate than the bioerodible substrate material and the bioerodible matrix material.

20. The medical device of claim 18, wherein said substrate is formed of a bioerodible substrate material, wherein said matrix material is formed of a bioerodible matrix material, and wherein said bioerodible material bioerodes at a faster rate than the bioerodible substrate material and the bioerodible matrix material.

* * * * *